United States Patent [19]

Svedman

[11] Patent Number: 5,358,494
[45] Date of Patent: Oct. 25, 1994

[54] IRRIGATION DRESSING

[76] Inventor: Pål Svedman, Östanväg 85 B, S-216 19 Malmö, Sweden

[21] Appl. No.: 121,892

[22] Filed: Sep. 16, 1993

Related U.S. Application Data

[63] Continuation of Ser. No. 793,377, filed as PCT/SE90/00441, Jun. 20, 1990, abandoned.

[30] Foreign Application Priority Data

Jul. 11, 1989 [SE] Sweden ................... 8902498

[51] Int. Cl.$^5$ ............................................. A61M 1/00
[52] U.S. Cl. ................... 604/313; 604/305; 604/316; 604/175; 604/36
[58] Field of Search ............... 604/21, 33, 36, 73, 604/93, 283, 175, 313, 316, 305; 128/887, 888

[56] References Cited

U.S. PATENT DOCUMENTS

| | | | |
|---|---|---|---|
| 3,026,874 | 3/1969 | Stevens | 604/305 |
| 3,398,743 | 8/1968 | Shalit | 604/36 |
| 3,753,439 | 8/1973 | Brugrolas et al. | |
| 3,874,387 | 4/1975 | Barbieri | |
| 4,250,882 | 2/1981 | Adair | 128/888 |
| 4,311,050 | 1/1982 | Bessman | 604/36 |
| 4,605,399 | 8/1986 | Westan et al. | 604/305 |
| 4,710,174 | 12/1987 | Moden et al. | 604/175 |
| 4,778,456 | 10/1988 | Lokken | 604/305 |
| 4,969,880 | 11/1990 | Zamierowski | 604/305 |
| 5,045,075 | 9/1991 | Ersek | 604/93 |
| 5,074,847 | 12/1991 | Greenwell et al. | 128/888 |
| 5,120,312 | 6/1992 | Wigness et al. | 604/93 |
| 5,176,663 | 1/1993 | Svedman et al. | 604/305 |

FOREIGN PATENT DOCUMENTS

| | | |
|---|---|---|
| 2809828 | 9/1978 | Fed. Rep. of Germany. |
| 0641061 | 8/1950 | United Kingdom ............... 604/305 |

Primary Examiner—Randall L. Green
Assistant Examiner—Paul Prebilic
Attorney, Agent, or Firm—Cushman Darby & Cushman

[57] ABSTRACT

An irrigation dressing for deep wounds comprises an adhesive, substantially liquid- and air-impermeable plate (1) having at least one perforation (6, 7) for supplying and sucking off liquid, and for pressure equalization. The perforation is provided with a conduit (10) for supplying and sucking off liquid. The conduit is introduced into the wound cavity, and irrigation liquid is supplied and sucked off through it. After completed irrigation, the perforation/perforations in the plate is-/are closed in order to seal the dressing.

A bag (18) can be connected to the dressing for filling up and actively affecting the wound cavity.

8 Claims, 3 Drawing Sheets

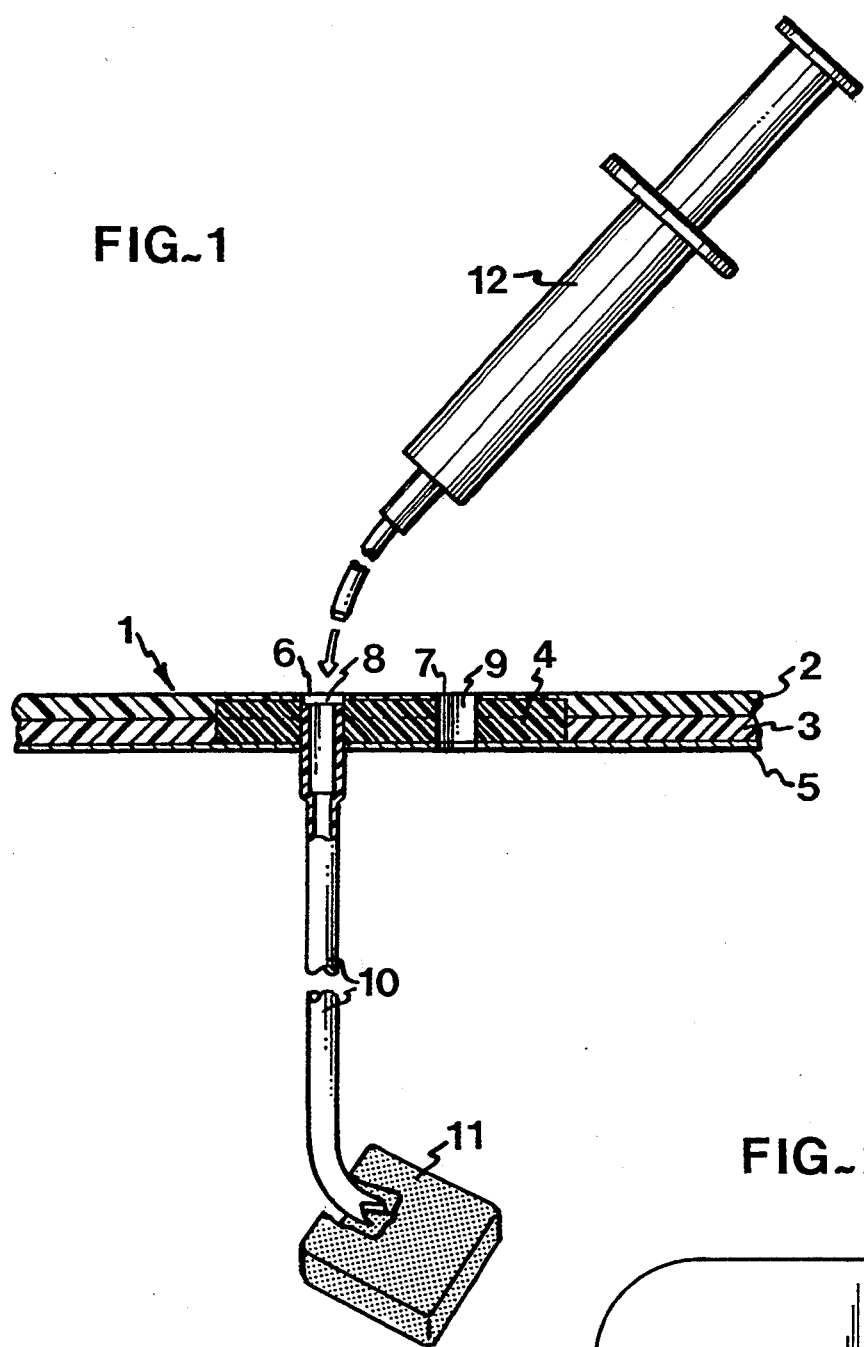
FIG._1
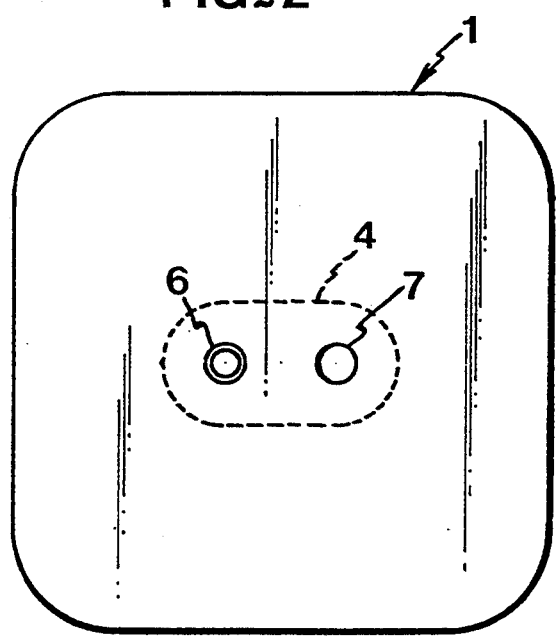
FIG._2

FIG._3
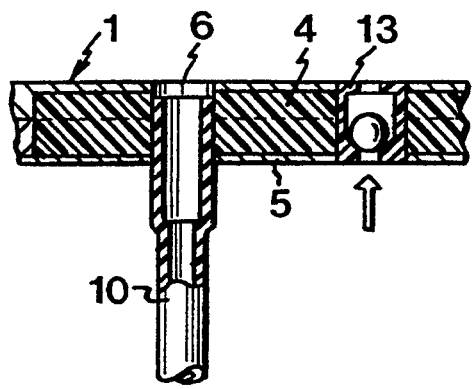
FIG._4
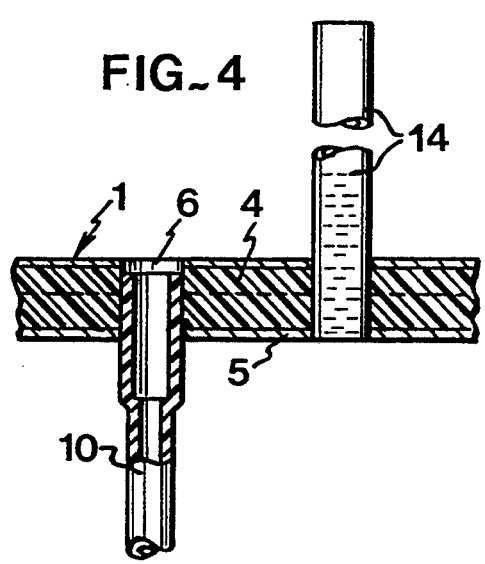
FIG._5
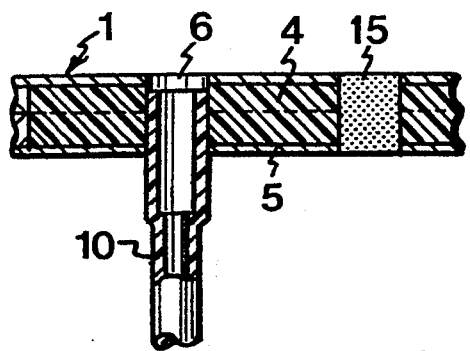
FIG._6
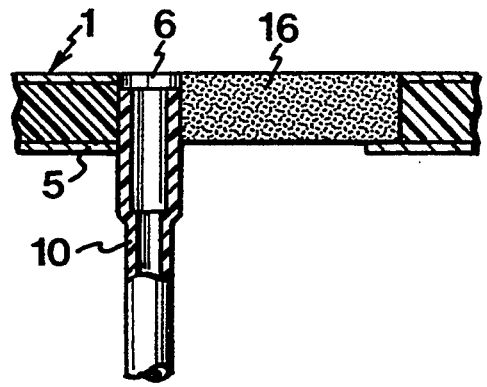
FIG._7
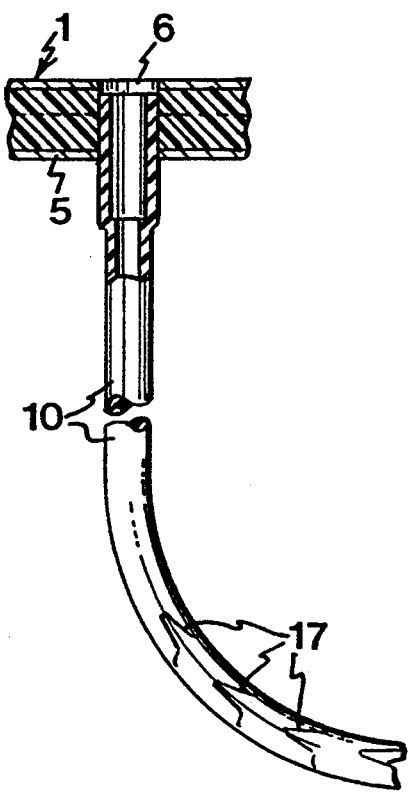

FIG._8
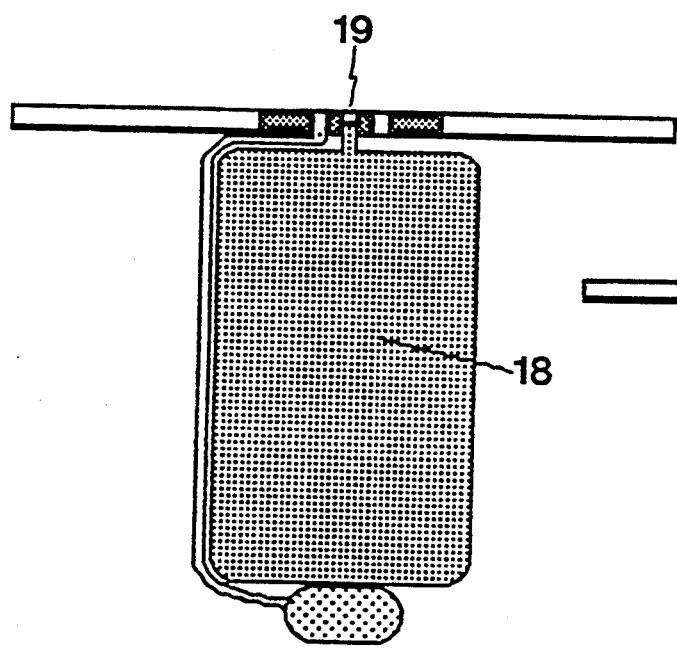
FIG._10a
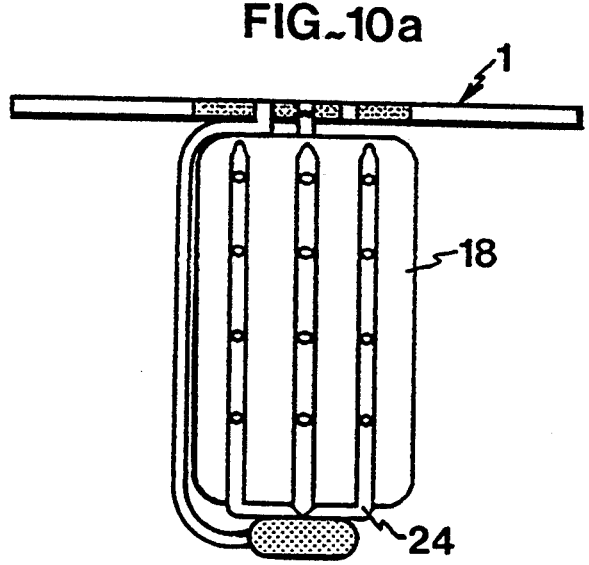
FIG._9
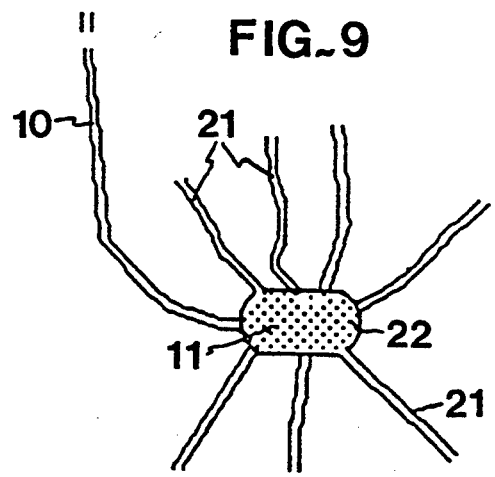
FIG._10b
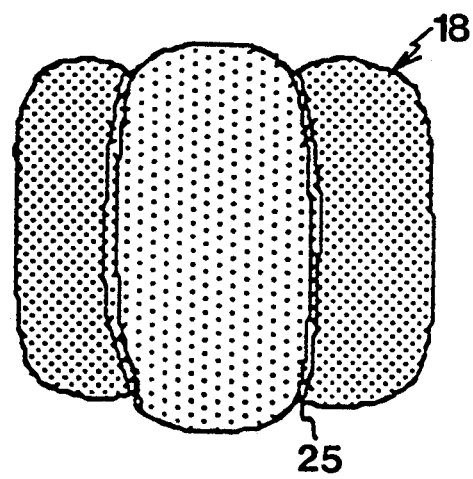

IRRIGATION DRESSING

This is a continuation of application Ser. No. 07/793,377, filed as PCT/SE90/00441, Jun. 20, 1990, which was abandoned.

The present invention relates to an irrigation dressing for deep wounds, which comprises an adhesive, substantially air- and liquid-impermeable plate having at least one perforation for supplying and sucking off liquid, and for pressure equalization.

In clinical care, deep wounds often become infected, which adversely affects the healing process and prolongs the nursing time of the patient. Actually, 2% of all elective and 10–12% of all emergency surgical operations are complicated by infections. Since these patients must be nursed for another 4–7 days at a cost of about SEK 1500 per day, it obviously is of the utmost importance that such infections be treated efficiently. Also pressure sores in patients with nerve injuries often get infected. Recently, the British National Health Service called attention to the fact that pressure sores cost the British Medical Service over SEK 900 million every year.

Local medical treatment provided at present consists in removing dead tissue, washing and irrigating the wounds. These are drained by means of rubber drains or packed with gauze compresses wetted with saline solution. Additional compresses are placed on top and covered with adhesive dressings. The compresses in the wound serve to support the walls of the wound cavity and, to some extent, immobilize the wound, relieving the pain of the patient. Also, they absorb liquid and pus from the wound, thus contributing to keeping clean the wound and the surrounding areas. On a small scale, foam rubber or the like can be used as filling. Such a material stimulates the development of a healthy wound surface. It takes a great deal of professional skill to "pack" a wound cavity in a proper way. One bandaging requires 15–30 min and may cause much pain to the patient. Furthermore, 6–7 bandagings may be needed every day. In large wounds requiring several compresses, a single compress may, if left behind in the wound, nourish the infection and enlarge the wound cavity U.S. Pat. No. 3,753,439, for instance, discloses a device for draining and irrigating infected wound cavities without any bandaging. This prior art device is, however, adapted for occasional draining and cannot be used as a dressing. DE 2,809,828, U.S. Pat. No. 3,026,874, U.S. Pat. No. 3,874,387, and U.S. Pat. No. 2,280,915, for instance, disclose devices for irrigating superficial wounds. When using the dressings disclosed therein, it is impossible to irrigate deep wounds and, furthermore, most of these dressings have a very complicated design. The methods disclosed in the above patents all suffer from practical inconveniences, making them unsuitable for clinical use.

Thus, there is a great need for an aid which improves and simplifies the treatment of deep wounds. This aid should be inexpensive and easy to handle, and should also alleviate pain.

One object of the present invention is to provide an irrigation dressing which can be used with all kinds of wound cavities regardless of their depth and which, also is inexpensive to manufacture.

Another object of the invention is to provide an irrigation dressing which can be handled by personnel with no special training and which does not prevent the patient from moving about freely.

Yet another object of the invention is to provide an irrigation dressing substantially reducing the number of redressings of the wound cavity, as compared with present-day techniques.

These objects are achieved by an irrigation dressing comprising a substantially air- and water-impermeable, flexible plate made up of an outer layer, an inner adhesive layer and, optionally, a release layer applied to the adhesive layer, said plate being formed with at least one perforation to which a conduit is connected for supplying and sucking off liquid, and which is also used for pressure equalization.

The invention will be described in more detail below with reference to the accompanying drawings which schematically illustrate embodiments of the invention and in which, FIG. 1 is a section of an irrigation dressing according to the invention;

FIG. 2 is a top plan view showing the outer surface of the inventive irrigation dressing;

FIGS. 3–6 are sections illustrating different embodiments of part of the inventive irrigation dressing;

FIG. 7 is a section of an embodiment of the conduit for supplying and draining liquid;

FIG. 8 is a section of another embodiment of the inventive irrigation dressing;

FIG. 9 illustrates an alternative embodiment of the conduit for supplying and draining liquid; and FIGS. 10a–b illustrate embodiments of a bag which can be connected to the inventive irrigation dressing.

FIGS. 1 and 2 illustrate the inventive irrigation dressing which comprises a flexible plate 1 which readily adapts to the skin and which is made up of an outer layer 2 and an inner adhesive layer 3. The outer layer is made of an air- and liquid-impermeable, flexible material, e.g. polyurethane foam, and the inner adhesive layer is, for example, made of a hydrocolloid adhesive material. The inner adhesive layer 3 is provided with a protective paper 5 which may, alternatively, form part of a package. At the center between the outer and the inner layer, there is a stiffened portion 4, e.g. of silicone. Alternatively, this portion may be provided on the top or bottom surface of the plate 1.

Two perforations 6, 7 are formed in the plate 1 and the stiffened portion 4, and connections 8, 9 are arranged in these perforations. A conduit 10 of flexible material that is kind to the skin and cannot be broken is fixed to the connection 8 in the perforation 6 for supplying and draining liquid. This conduit is, for instance, a thick-walled silicone hose. The lower end of this hose may be cut off squarely, but it suitably has a pointed end, which facilitates the use of the hose. Furthermore, a flexible pad 11, e.g. a cylindrical piece of synthetic fabric or foam rubber forming an open-pore capillary system, is arranged at the lower end of the hose. The pad, which is passed over the end of the conduit, can fill up more or less of the space in the wound cavity. The conduit 10 either has a given length or is provided with weakened portions or rupture lines 17 at different levels, so that it can be torn off to a suitable length. This is illustrated in FIG. 7.

The outer layer 2 of the plate 1 as well as the conduit 10 and the rigid portion 4 may consist of silicone, polyvinyl chloride plastic, or any other suitable plastic or rubber.

The perforation 7, together with the associated connection 9, has pressure-equalizing function. Here, air passes freely. The perforation 7 is not necessarily equipped with a connection, but may consist of a through bore. If a connection is arranged in the perforation 7, it may alternatively be equipped with a water seal 13 (see FIG. 3) or, if there is not sufficient room within the narrow perforation area, with a water seal device (not shown) which is only momentarily connected to the connection and then removed. Yet another alternative is attaching to the connection a water-level indicator 14, e.g. a transparent rubber hose, as shown in FIG. 4. Thus, it is possible to see when the wound cavity has been filled with irrigation liquid and sucking-off should begin. As is apparent from FIG. 5, the perforation 7 can be equipped with an air filter 15 for keeping out bacteria. As shown in FIG. 6, it is possible to provide in the plate 1, instead of the perforation 7, an area 16 of porous, air-permeable material, which replaces the outer impermeable layer and the adhesive layer and, thus, performs a pressure-equalizing function. The porous material Then suitably has a water-repellent surface on the side facing the skin. Moreover, both connections 8 and 9 are suitably adapted to be connected to existing systems in hospitals.

To avoid any projecting or otherwise obstructing parts, the connections 8 and 9 are suitably countersunk in the outer surface of the outer layer 2, i.e. on the side opposite to the side attached to the adhesive layer. The stiffened plate portion 4 can be dispensed with if the dressing is stable enough without it. Before use and after irrigation and draining, the two connections can be closed by means of a piece of adhesive tape or, for example, a lid of silicone plaster.

On the side facing away from the side of the hose, the perforation 6 and the connection associated therewith are adapted to be connected to e.g. a syringe 12 (see FIG. 1) for supplying irrigation liquid to and also draining the wound cavity. In the case of large wound cavities, it may be necessary to rely on drip to fill the cavity. In that case, the connection can be coupled to a two-way valve with an associated syringe for draining the cavity. With the syringe, liquid is then sucked off from the cavity one way and pressed out the other way.

Alternatively, the plate 1 can be formed with only one perforation for supplying and sucking off liquid as well as for pressure-equalization. This could be done by the conduit 10, which is connected to the perforation, being a double conduit or by the air from the wound cavity being allowed to pass beside the conduit.

FIG. 8 illustrates yet another embodiment of the inventive irrigation dressing. This dressing comprises an impermeable bag 18 which is used for filling up the wound cavity. The bag, which is to be wholly or partly filled, either with liquid, such as water, or with gas, such as air, adapts to the shape of the walls of the wound cavity after being filled. Using this bag, compresses or other filling materials may not be needed. Usually, the bag is elastic and made of polymer materials, optionally foam material or latex rubber, but it may also be inelastic. Not only does the bag lend support and contribute to immobilization, but the foreign material thereof may also stimulate the healing process. In this case, the plate 1 is formed with yet another opening 19 for the connection and refilling of the bag 18. The opening 19 may, for instance, be provided with a rubber membrane. This embodiment further facilitates the bandaging of the wound for both the patient and the personnel. Advantageously, the irrigation according to the invention will only involve the layer between the bag and the wound surface.

The bag 18 may also have an active function. The bag wall may, for instance, consist of a semipermeable membrane allowing e.g. pharmaceutical preparations to pass from the interior of the bag which is filled with liquid. Alternatively, the bag wall may be provided with a pharmaceutical preparation, other healing substances, bactericide or the like. To facilitate sucking off liquid from the wound cavity after the liquid level has reached the plate 1, the bag wall facing the wound surface may have open communicating tubes or ducts 24 (see FIG. 10a) serving to distribute and drain liquid towards the pad 11 or the opening of the conduit 10. Instead of separate ducts, the bag may, as shown in FIG. 10b, have constrictions 25 entailing the formation of ducts between the bag wall and the wound surface. These constrictions may be produced by the bag material having lower resilience at 25. Also, a capillary-active material, e.g. a woven fabric, can be applied to the outer bag wall surface to facilitate the draining of irrigation liquid. Another alternative is to design the bag 18 with double walls, such that liquid ducts are formed in the layer between the outer and the inner wall. Also in this case, the outer wall may be made of either a semipermeable material allowing the passage of e.g. pharmaceutical preparations, or a capillary-active material. Furthermore, the ducts may be wholly or partly perforated, and the bag may be formed, wholly or partly, with ducts while at the same time comprising both capillary material and semipermeable material. The bag 18 may also serve substantially as a stabilizer after the irrigation. In this case, the bag can be used not only with the inventive irrigation dressing, but also with another separate plate or an adhesive layer. By being a foreign material in the wound, the bag stimulates the healing process. To further facilitate the introduction of the bag, the connection between the plate 1 and the bag 18 may be extended by a hose.

FIG. 9 illustrates an embodiment of the lower part of the conduit 10. This embodiment is particularly suited for use in the case of bag-equipped dressings. In this case, the end of the conduit which is to be placed in the deepest part of the wound is equipped with a pad 11 having communicating or non-communicating chambers or ducts 22 which have a capillary or non-capillary function. Optionally, the pad has stabilizing means keeping the ducts open to external or internal pressure. The chambers or ducts of the pad are open outwards and to the conduit 10 and may communicate with flexible tubes 21 optionally formed with perforations on a major or minor part of their surface. These tubes are distributed across the wound surface, and liquid from the wound, as well as irrigation liquid, is drained to the pad through the tubes between the bag and the wound surface. Alternatively, the pad consists of a more rigid member, e.g. of plastic that is kind to the skin, having a plurality of holes for distributing irrigation liquid across a larger area.

In the above embodiments using the bag 18, the conduit 10 is arranged beside the bag. It is to be understood that the conduit 10 may just as well pass through the bag 18.

The irrigation dressing according to the invention operates as follows. The conduit 10, and optionally the pad 11 at the end of the conduit, is placed in the deepest part of the wound cavity to be treated, whereupon the remainder of the cavity is filled with gauze compresses. If the embodiment with the bag 18 is instead used, the bag is filled to a suitable extent and then placed in the wound cavity for final adjustment of its volume. The plate 1 is then applied over the wound cavity with the adhesive material facing against the skin, and when the plate is in position, the system is sealed, the connections 8 and 9 excepted. In the irrigation treatment, the wound surface is always turned upwards so that the cavity can be completely filled. The conduit and the pad then are located in the deepest part of the wound. In case the wound cavity is not very large, a syringe is connected to the connection 8 and irrigation liquid is supplied to the cavity until there is an indication that the cavity is filled. Then, the cavity is drained, the syringe is removed, and the connections are closed. The pad 11 serves to absorb also the liquid at the bottom of the wound cavity, which is not possible to do with only a hose end. After the sucking-off, the compresses in the wound cavity are saturated with liquid to about 50%.

The invention is illustrated by the following Examples which are however by no means restrictive thereof.

EXAMPLE 1

Irrigation of a small cavity, below 50 ml (e.g. a drained abscess)

A filled 50 cm$^3$ syringe is applied to the connection with the conduit. Liquid is injected until there is a resistance, when the water seal closes or the indicator shows that the cavity is filled. Then, the syringe is used for sucking off not only the injected liquid, but also pus and bacteria present in the wound before the irrigation. The syringe and the water seal or indicator, if any, are then disconnected. The connections are sealed to achieve occlusive conditions in the wound until the next irrigation is to take place. When the cavity is filled with gauze compresses, the liquid flow in the capillary-active gauze material, as well as in the woven fabric, is conducted under suction towards the pad. The gauze is washed of pus, which reduces the need of bandaging.

EXAMPLE 2

Irrigation of a large cavity, above 50 ml (e.g. a bedsore)

A dropping bag with associated equipment is applied to the connection with the conduit. The wound is filled as in Example 1. Then, the equipment is disconnected, and a syringe with a two-way valve is connected. The liquid drained is conducted to a urine drainage bag or a plastic bag. Several aspirations are performed until the cavity is drained of liquid.

With the inventive irrigation dressing, only one bandaging is needed every day instead of 3–7, this relieving the patient of both physical and mental suffering, and also saving the medical service considerable amounts of money. Furthermore, the inventive irrigation dressing is extremely easy to handle and therefore requires no specially-trained personnel. It is even conceivable that the patient may himself handle the dressing. Since there are no projecting parts on the dressing when it is not used for irrigation, the dressing is indeed suitable for patients with bedsores, and it also enables the patient to move about freely. The dressing can be used in both small and large wound cavities. Especially when the conduit is provided with weakened portions or rapture lines and when the bag is attached thereto, the dressing is readily adapted to a particular cavity.

I claim:

1. An irrigation dressing for deep wounds comprising a substantially air- and water-impermeable, substantially flat and flexible plate (1) comprising an outer layer (2), an inner adhesive layer (3) and, optionally, a release layer (5) applied to the adhesive layer, said plate being formed with at least one perforation (6) to which one end of a conduit (10) is connected for supplying and removing liquid, and which is also used for pressure equalization, an opposite end of the conduit (10), which is to be placed in the wound, being provided with a pad (11) of capillary-active material such that said pad (11) is provided at a distance from the plate (1); and the pad (11) being provided with ducts (22) and outlet tubes communicating therewith.

2. An irrigation dressing for deep wounds comprising a substantially air- and water-impermeable, substantially flat and flexible plate (1) comprising an outer layer (2), an inner adhesive layer (3) and, optionally, a release layer (5) applied to the adhesive layer, said plate being formed with at least one perforation (6) to which one end of a conduit (10) is connected for supplying and removing liquid, and which is also used for pressure equalization, an opposite end of the conduit (10), which is to be placed in the wound, being provided with a pad (11) of capillary-active material such that said pad (11) is provided at a distance from the plate (1); and a bag (18) for filling up the wound cavity, the plate being formed with an additional opening (19) for connection and refilling of said bag.

3. An irrigation dressing for deep wounds comprising a substantially air- and water-impermeable, substantially flat and flexible plate (1) comprising an outer layer (2), an inner adhesive layer (3) and, optionally, a release layer (5) applied to the adhesive layer, said plate being formed with at least two perforations (6; 7) to one end of one said perforation (6) of which a conduit (10) is connected for supplying and removing liquid, and an other said perforation (7) is used for pressure equalization, an opposite end of the conduit (10), which is to be placed in the wound, being provided with a pad (11) of capillary-active material such that said pad (11) is provided at a distance from the plate (1); and a portion of the plate (1) around said at least two perforations (6; 7) is made of a porous, air-permeable material (16) which, on the side facing the skin optionally has a water-repellant surface.

4. An irrigation dressing for deep wounds comprising a substantially air- and water-impermeable, substantially flat and flexible plate (1) comprising an outer layer (2), an inner adhesive layer (3) and, optionally, a release layer (5) applied to the adhesive layer, said plate being formed with at least one perforation (6) to which one end of a conduit (10) is connected for supplying and removing liquid, and said at least one perforation is also used for pressure equalization, an opposite end of the conduit (10), which is to be placed in the wound, being provided with a pad (11) of capillary-active material such that said pad (11) is provided at a distance from the plate (1); and the conduit (10) has weakened portions (17) for facilitating shortening the conduit (10) to a desired length.

5. An irrigation dressing for deep wounds comprising a substantially air- and water-impermeable, substantially flat and flexible plate (1) comprising an outer layer (2), an inner adhesive layer (3) and, optionally, a release layer (5) applied to the adhesive layer, said plate being formed with at least two perforations (6; 7) to one end of one said perforation (6) of which a conduit (10) is connected for supplying and removing liquid, and an other said perforation (7) is used for pressure equalization, an opposite end of the conduit (10), which is to be placed in the wound., being provided with a pad (11) of capillary-active material such that said pad (11) is provided at a distance from the plate (1); and connections (8, 9) arranged in the respective perforations (6, 7) and countersunk in a surface of the plate that is opposite to the surface attached to the adhesive layer (3).

6. An irrigation dressing for deep wounds comprising a substantially air- and water-impermeable substantially flat and flexible plate (1) comprising an outer layer (2), an inner adhesive layer (3) and, optionally, a release layer (5) applied to the adhesive layer, said plate being formed with at least one perforation (6) to which one end of a conduit (10) is connected for supplying and removing liquid, and said least one perforation is also used for pressure equalization, an opposite end of the conduit (10), which is to be placed in the wound, being provided with a pad (11) of capillary-active material such that said pad (11) is provided at a distance from the plate (1); and a bag for filling up and, optionally, actively affecting a wound cavity, said bag being defined by a wall and having a connection for filling it, said bag being completely or partly filled with liquid or gas.

7. The irrigation dressing as claimed in claim 6, wherein said bag has two walls.

8. The irrigation dressing as claimed in claim 6, wherein the the bag is provided with a pharmaceutical preparation.

* * * * *